United States Patent [19]

Hurd et al.

[11] Patent Number: 4,913,791

[45] Date of Patent: * Apr. 3, 1990

[54] BLOT FRAME AND METHOD OF HANDLING

[75] Inventors: Stanley M. Hurd, Hamden; Richard E. Kouri, New Haven, both of Conn.

[73] Assignee: Bios Corporation, New Haven, Conn.

[*] Notice: The portion of the term of this patent subsequent to Mar. 14, 2006 has been disclaimed.

[21] Appl. No.: 317,423

[22] Filed: Mar. 1, 1989

Related U.S. Application Data

[62] Division of Ser. No. 90,739, Aug. 28, 1987, Pat. No. 4,812,216.

[51] Int. Cl.$^4$ .............................................. G01N 27/28
[52] U.S. Cl. .............................. 204/299 R; 204/182.8
[58] Field of Search ......................... 204/299 R, 182.8

[56] References Cited

U.S. PATENT DOCUMENTS

| | | | |
|---|---|---|---|
| 4,709,810 | 12/1987 | Mayes | 206/205 |
| 4,759,838 | 7/1988 | Mayes | 204/299 R |
| 4,812,216 | 3/1989 | Hurd | 204/182.8 |

Primary Examiner—John F. Niebling
Assistant Examiner—Isabelle Rodríguez
Attorney, Agent, or Firm—Bachman & LaPointe

[57] ABSTRACT

A method and apparatus is disclosed for supporting and handling blot membranes during the course of blotting, analysis and storage.

10 Claims, 2 Drawing Sheets

BLOT FRAME AND METHOD OF HANDLING

This is a division of application Ser. No. 090,739, filed Aug. 28, 1987, now U.S. Pat. No. 4,812,216, issued Mar. 14, 1989.

RELATED APPLICATIONS

Ser. No. 051,761, filed May 20, 1987, by Hurd et al., entitled A Method and Apparatus for Molding Thin Gel Slabs Horizontally with Integrally Molded Large Volume Sample Wells, now U.S. Pat. No. 4,795,541, and an application filed Aug. 28, 1987, by Hurd et al., entitled Method and Apparatus for Blotting From Electrophoresis Gels, now U.S. Pat. No. 4,818,360.

BACKGROUND OF THE INVENTION

Many of the procedures commonly used in molecular biology involve the generation and analysis of blots from DNA, RNA, protein samples, or other biological components. These blots consist of thin sheets of nitrocellulose, charged nylon, or the like, to which the samples species to be studied are bound by any of a number of procedures. The sheets provide support for the sample species and allow the researcher to visualize and analyze the species of interest in a more convenient, albeit somewhat cumbersome, manner.

The current techniques used to generate and analyze these blots have been largely adapted from other procedures, and little effort has been made to create an efficient system to support these activities in a more dependable fashion. In the classical procedure, the sample to be studied is first separated on the basis of its size using gel electrophoresis. The sample is then driven out of the gel and onto the nylon or nitrocellulose membranes transfer membranes by fluid flow (Southern, E., J. Mol. Biol. 98:503, 1975) or by electrical current (see, e.g., Kreisher, J. H., U.S. Pat. No. 4,589,965, 1986). These procedures are collectively called blotting and the resultant membrane with the sample species affixed to it is called a blot. Usually the blot is then heated or treated with ultraviolet radiation or other means to cause the sample species to bind covalently to the membrane support matrix. The blot is then ready to be used in the study of the species that has been attached to it.

In conventional blotting procedures, unsupported transfer membranes are first layered on top of the gels by hand, and then the gel and membrane together are sandwiched in the blotting apparatus. Since these steps are performed manually, it is difficult to place an unsupported membrane upon a gel accurately to insure even or uniform transfer of the material from the gel to the membrane. It is even more difficult to duplicate membrane placement accurately and consistently from gel to gel. This problem results in a good deal of variability in the resulting configuration of the blots, making it difficult to compare successive blots directly. In addition, these prior art techniques are time-consuming, requiring at least 12-14 hours for capillary transfer and 2-4 hours for electroblotting. Electroblotting also requires costly power supplies and transfer chambers, as well as large quantities of buffer.

The next step in the analysis of the blots, called hybridization or visualization, uses a probe to bind to certain select species on the blot. The probe is labeled, usually with radioisotopes, so that desired fragments can be imaged subsequently to give a permanent record of the results. In the commonly used procedures, the blots are placed in plastic bags, and the radioactive probe solution is added. All air bubbles are removed by hand; then the bag is heat-sealed. The bag is then incubated in a water bath for an appropriate time, after which the blot is removed and rinsed several times to remove any probe that has not bound to its specific target species. These steps are labor-intensive and cumbersome (the researcher must work behind a safety shield), and inevitably result in contamination of the surroundings with radioactivity.

Certain commercial products have been introduced to carry out hybridization with greater facility. Hybrid-Ease TM (Hoefer Scientific Instruments, San Francisco, Calif.) and Turbo-Blot TM (American Bionetics, Malvern, Pa.) are examples of such devices. While they are significantly better than the sealable plastic bags, each has certain shortcomings. Hybrid-Ease has a very large incubation chamber, that requires 3-6 times the volume of probe solution required by the plastic bags. The probes are very costly and must be at fairly high concentration in the hybridization solution; this is a serious drawback. The Turbo-Blot unit is little more than a plastic bag with tubing fittings to introduce the solutions and clamps to seal the bag. It is complicated to set up and use, and also requires considerable volumes of probe solution. Neither of these units is designed to work in conjunction with or configured to facilitate transition from preceding to successive steps in the generation and analysis of the blots. That is, there is no convenient blot support means, blot frame structure, blot handling apparatus or smooth sequential procedure for accomplishing and facilitating successive steps.

Next the bound, radiolabeled probe on the blot is imaged by placing the blot against an x-ray film for a period of 10-72 hours. Since it is not often possible to ascertain before-hand how much radioactivity has bound to the blot, it is not possible to pre-determine the correct exposure time. It is thus common prior art practice to use two X-ray films, one on either side of the blot. This "sandwich" is taped onto the inside of a light-tight container. After an appropriate time, the outer film is removed and developed. If it is not fully exposed, the second film is left in place for an additional period of time. However, during the removal of the first film the blot is often shifted in relation to the second film, causing a blurred image. This cumbersome process is made more difficult because of the fact that these steps of necessity are performed in a darkroom and the blot itself is really just a thin piece of membranous material and is therefore difficult to handle. The problem is exacerbated when one realizes that the radioactivity itself is decreasing rapidly because of the natural halflife of the isotopes. For example, the most commonly used radioactive isotope, phosphorus 32, has a halflife of only 14 days. Thus, if the imaging step has to be repeated, the amount of isotope that is present and the amount of time required to detect this radioactivity are both different from that observed the first time.

Finally, even though prior art blots may be reused a number of times, they are difficult to store because they are quite susceptible to contamination (one fingerprint will often hold more DNA than resides on an entire blot) and physical damage. It is difficult to protect these membranes from such contamination since the contaminants are rather ubiquitous, so that any storage package will likely have in it significant levels of contaminants. In addition, certain types of membranes become brittle with use, making them very fragile and difficult to handle without peripheral support. For these reasons, storage of the blots in most conventional media such as paper or plastic envelopes or boxes is often unsatisfactory.

SUMMARY OF THE INVENTION

It is therefore the general object of this invention to provide a system by which the steps involved in the generation, analysis, storage, and handling of blots may be accomplished with greater efficiency and efficacy.

It is a specific object of this invention to provide a means and a method for transporting blot or transfer membranes between the steps of blotting, hybridizing, imaging, and storage such that the placement and orientation of the blot in each of these steps will be highly reproducible and uniform.

It is a further object to provide a transfer membrane support means.

It is a still further object of the invention to provide a supported membrane by molding a plastic frame about the periphery of a taut membrane.

It is a further object of the invention to provide a process for generating a supported membrane by providing a mold cavity; using a membrane as a mold insert and thereafter introducing thermoplastic material into the mold cavity to produce a supported membrane as a unitary article.

It is a further object of this invention to provide a means by which a blot membrane may be juxtaposed to an electrophoresis gel expeditiously and with a consistent and reproducible placement from membrane to membrane.

It is another specific object of the current invention to provide a means by which hybridization may be carried out with less labor, less radioactive contamination, and using low volumes of probe solutions.

It is a further object of this invention to provide a rapid and efficient method for the juxtaposition of two x-ray films to the hybridized blots.

It is yet another object of the present invention to provide a means for the storage of blots in such a way that they may be easily protected from contamination and physical damage.

It is a still further object of the invention to provide a framed membrane where the frame portion is coated with a non-wettable material to keep liquid, such as hybridization probe solution, from migrating over the frame portion by capillary action.

A further feature of the invention is that the membrane support means or frame structure, by virtue of its rigidity, makes it possible to use membrane materials which in prior art procedures presented handling problems because of their friable, cleavable or brittle nature.

A method embracing certain principles of the present invention may comprise the steps of providing a membrane, providing a support means, securing the membrane to the support means by a suitable adhesive, by interlocking two piece frame members, or by molding the frame about the periphery of the membrane, whereby the membrane is handled conveniently via the support means without risk of disturbing the membrane or biological material bound to the membrane.

An apparatus embracing certain other principles, of the invention may comprise membrane support means in combination with at least one receptacle where the support means and the receptacle are provided with cooperating, releasable lock or key means to insure that each support means and its accompanying membrane are received in the same orientation from receptacle to receptacle.

Other features and advantages of the present invention will become more apparent from an examination of the succeeding specification when read in conjunction with the appended drawings; in which,

DESCRIPTION OF THE PREFERRED EMBODIMENT

The present invention resides in the use of a carrier piece, or frame, that may be used to support the blot membrane and give it a uniform shape and mechanical rigidity. The use of such a carrier member or support means brings significant benefits to each of the steps outlined above, and provides the means by which these steps may be coordinated into an efficient system for the generation and analysis of the blots. No such system has been previously described. In addition, the use of such a carrier member will allow for the generation of an automated system by which a supported membrane can be handled mechanically to carry out various procedures in a step-by-step fashion. Such an automated system would be very difficult to achieve without the use of a carrier member or support means to support the membranes and move them from one step or location to another.

In the blotting step itself, wherein the sample species are transferred from the electrophoresis gel to the membrane, the use of a framing member greatly simplifies the placement of the membrane next to the gel. Moreover, by providing a suitable lock-and-key arrangement between the frame and blotting apparatus, it is possible to produce blots with well-defined and reproducible geometries. This is important in that during handling of unframed prior art blots, it is difficult to follow or read the blot geometry because of the inevitable side-for-side and end-for-end rotations, reversals or turns that unsupported blots undergo. In contrast, in an automated or integrated system the rigidity imparted to the membrane by a support means or a frame, in combination with the lock-and-key feature, insures reproducible placement of membranes enhancing greatly the integrity of the blot.

A further benefit of the framing member to the blotting step derives from the fact that it is an absolute requirement that the membrane not be shifted in relation to the gel once the membrane and its gel are placed in contact with each other. This is because the sample species in the surface layers of the gel transfer move very rapidly to the membrane as soon as contact is made. If the gel and membrane are shifted relative to one another after the initial contact, the resulting blot will be blurred and difficult to interpret. The use of a rigid frame member with suitable lock-and-key features eliminates this possibility. Again, the framing member increases the quality and reproducibility of the blots.

Figure 1:
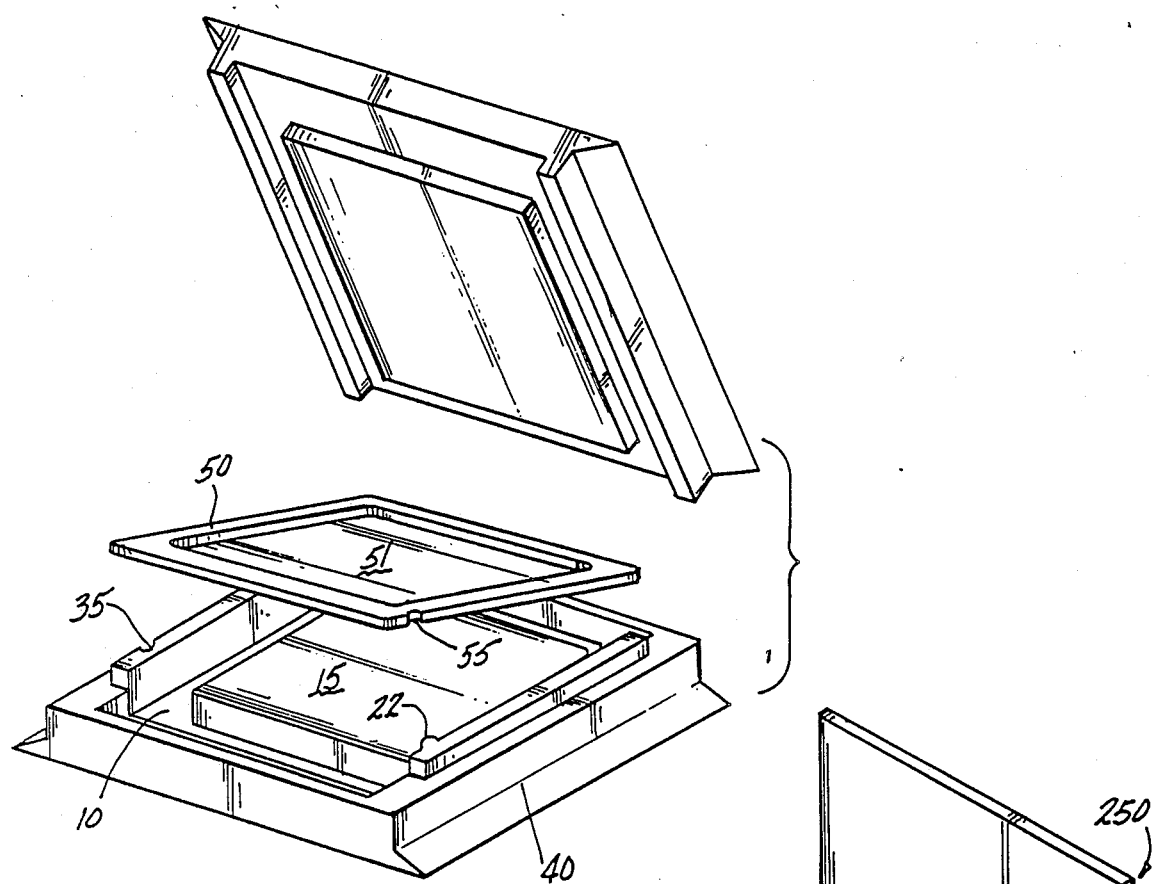
FIG. 1 is an exploded view in perspective of a supported blot membrane poised for blotting contact with a gel slab.

FIG. 1 illustrates the use of a framed blot membrane in a blotting application. In this technique, a thin (less than 1.5 mm thick) electrophoresis gel 15 is cast and run on gel tray 10 (see U.S. Pat. No. 4,795,541). The gel tray is received in base 40 of the blotting unit with its alignment fixed by engagement of groove 35 on gel tray 10 with a mating projection (not shown) in base 40. Membrane 51 having support means defined by peripheral frame 50 is placed on top of the gel. Projection 22 of the gel tray mates with groove 55 of the blot frame 50 in order to orient blot frame 50 securely and reproducibly in relation to the gel. Blot frame 50 is constructed of a strong, inert material such as nylon, sulfonated polystyrene, polycarbonate or other suitable materials. Membranes may be single ply fabricated from various materials such as nitrocellulose, charged or uncharged nylon or the like, or may be laminates thereof.

For purposes of claiming the present invention the grooves and projections collectively are termed keying or locking means, defining, specifically, a first keying means (groove 35 and mating projection not shown) and a second keying means (groove 55 and mating projection 22).

Figure 4:
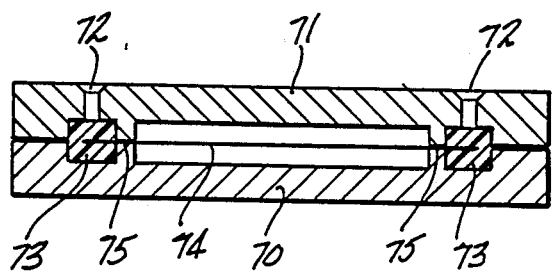
FIG. 4 is a vertical section of a mold cavity for molding a frame structure about a membrane where the membrane is a mold insert.

FIG. 4 shows a vertical section of a mold cavity having a bottom plate 70 and a top plate 71 formed with sprues 72—72 for admitting suitable thermoplastic resins into mold cavity 73 operable to mold a frame about the periphery of a membrane 74 defining a mold insert. The membrane is held tautly between flats 75—75 and the molding operation results in a frame member molded integrally with the membrane to define a unitary piece part. Depending upon the processing temperature of the resin used to mold the frame relative to the temperature sensitivity of the membrane material it may be necessary to core portions of the mold body for coolant to avoid degradation of frame resin or the membrane material.

The general benefits of the blotting device and procedure illustrated in FIG. 1 are described in said '541 patent and U.S. Pat. No. 4,818,360. As stated previously, the use of a membrane support means or the frame member provides a degree of rigidity that makes it markedly easier to blot from thin gels. The use of an unframed membrane would of necessity subject the thin gels to a significant degree of handling or disturbance as the membrane is aligned on the gel. This occurrence would greatly increase the probability that the gel would be torn or contaminated. Therefore, the use of the framed member enhances the utility of the devices and procedures given in the above-referenced '541 application. The use of a framed membrane also makes it significantly easier to exclude air pockets from between the gel and membrane by the simple expedience of lowering the framed membrane at an angle to the surface of the gel contacting the gel initially at one end and gradually rotating the framed membrane about said end until full a real or face-to-face contact is achieved between the gel surface and the membrane. The ease and rapidity with which framed membrane can be placed upon a gel is of particular importance in blotting from thin gels. In such gels, the deleterious effect of moving the gel in relation to the membrane after initial contact, as described above, is greatly increased. Further, it can be appreciated that, inasmuch as the frame couples the blotting step to the subsequent steps of hybridization, imaging and storage, as described hereinafter, and the blotting apparatus and procedure of said '360 patent is coupled to the electrophoresis step by the apparatus and procedure of said '541 patent, a completely integrated system for the generation and analysis of blots can now be described. Such an integrated system is a necessary first step for the automation of these procedures.

As stated previously a supported or framed blot facilitates the transfer of the blots between successive steps. By providing a uniform, relatively rigid support means to handle the blot without contaminating it or subjecting it to mechanical stress, the efficiency of the various procedures or steps and the lifetime of the blots is increased. This feature is critical in automated systems, since conventional prior art handling techniques such as roller-feeds or tractor-feeds are ill-suited to unsupported membranes, particularly when the membranes are wet. In addition, the frame provides a good surface for permanently labeling or identifying the blots. This may be done readily without the risk of contaminating them in the process.

The use of a frame also provides an unexpected benefit in the hybridization step. In this step a target molecule, or probe, which binds to a specific species on the blot, is placed on the membrane to visualize that species. Often the probe will be made radioactive to provide the means of visualization. Because the membrane is stretched tautly in the frame, the hybridization medium can be applied directly to the membrane. This means that the absolute minimum volume needed to wet the membrane can be used, without the need for additional volume to fill a container as required by current prior art procedures. Again, a lock-and-key fit between the hybridization chamber and the blot frame (third keying means) ensures that the probe solution is applied to the same side of the blot to which the sample species was bound, initially.

After hybridization the blots must be washed repeatedly to remove all non-specifically bound probe. The framing member provides benefits to this process in two ways. First, the taut surface is much better suited for the laminar flow of the washing buffers over the membrane than an unsupported membrane. Therefore, in any washing procedure in which the washing buffers are caused to flow past or swirl around the membranes, the framed membrane will be washed more efficiently and more rapidly than will be an unsupported membrane. The second benefit is that, by virtue of the fact that the frame holds the membrane away from contact with any container walls in the washing apparatus, the buffers will have free access to all portions of the membrane. In this way, no dead zones of restricted buffer flow will be present to cause uneven washing. Both of these benefits serve to create a higher-quality blot with lower and more even background interference.

Figure 2:
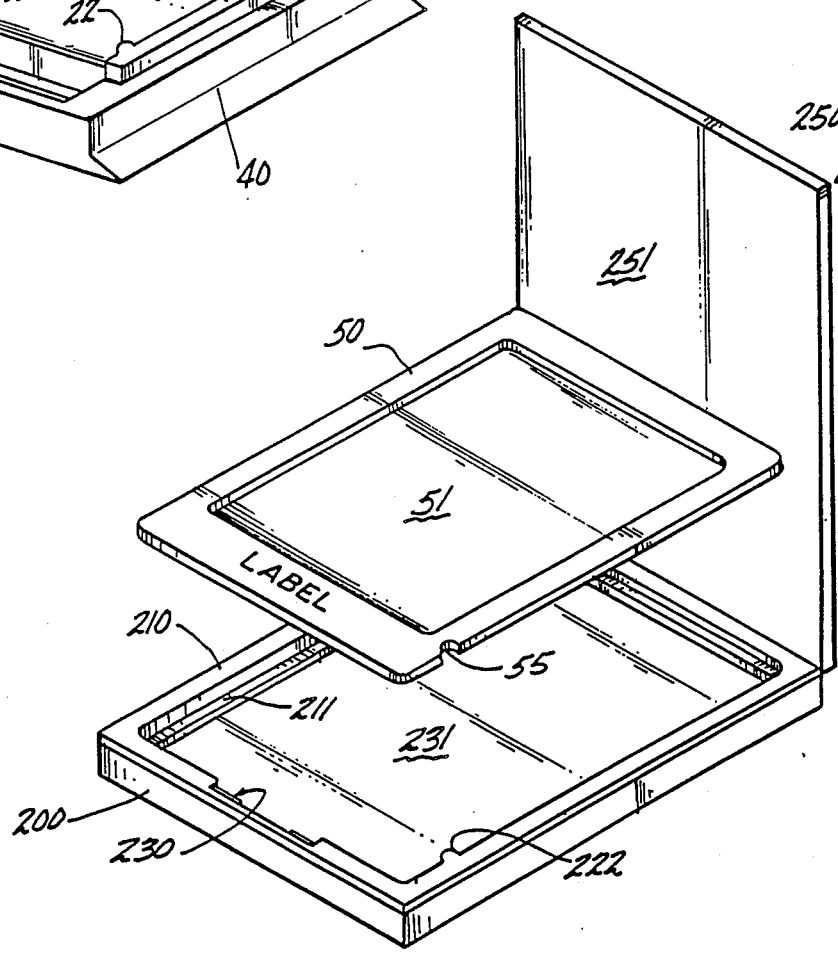
FIG. 2 is an exploded view showing the supported blot membrane at the hybridization station.

FIG. 2 illustrates the use of a framed membrane in a hybridization application. In the figure, blot frame 50 is positioned in hybridization cassette or chamber 200. Hybridization cassette 200 is constructed of a rigid, inert and radio-opaque material such as acrylic plastic. This material will protect the user from radiation sources within the cassette. It is provided with gasket 210 or other such means to provide a water-tight seal with lid 250. This prevents evaporation of the probe solution during hybridization. Frame 50 is pressed down past resilient or spring pressed button 230 (bottoming on shoulder 211) to hold the framed membrane securely in cassette 200, so that the membrane will not move during handling. Since frame 50 holds membrane 51 level and taut, suspended free of bottom surface 231 and top surface 251 of cassette 200, there can be no points of contact that would create dead zones where the concentration of radioactive probe solution would be lower than the surrounding areas. Furthermore, it is unnecessary to fill the cassette with probe solution as is done in the Hoefer and ABN units described earlier. The result of this is that the absolute minimum amount of probe solution required to wet membrane 51 completely is all that is needed to carry out hybridization. For a typical 20×20 cm membrane, this would be a total volume of approximately 8 ml. This may be contrasted with a widely-used procedure in which a 20×20 cm membrane in a plastic bag would have a minimum of 28 ml (see Maniatis, T., et al., *Molecular Cloning: A Laboratory Manual,* Cold Spring Harbor Laboratory Publications, Cold Spring Harbor, N.Y., 1982). It will be readily appreciated that, by concentrating the probe solution more than three-fold, the hybridization reaction will be significantly faster and be more efficient in terms of the amount of radioactivity required to provide a strong image. This volume also compares favorably to the commercially available units, which range in required volume between 28–50 ml.

It may be desirable in some cases to coat the frame 50 with a non-wettable material such as dimethyldichlorosilane to preclude migration of probe solution over the frame via capillary action. Such coating would prevent the probe from binding non-specifically to the frame and obscuring the results of the hybridization. Alternatively, the frame can be constructed from a non-wettable material such as Teflon TM or Delrin TM.

In the imaging step, the use of a rigid framing member obviates the need for taping the film and blot together. Using an appropriately shaped cartridge or container, the film can be clamped to the blot without the use of adhesives or tape. By clamping film on either side of the blot, it is possible to follow the normal procedure of removing one film prior to the other, without disturbing the relative positions of the blot and the second film.

Figure 3:
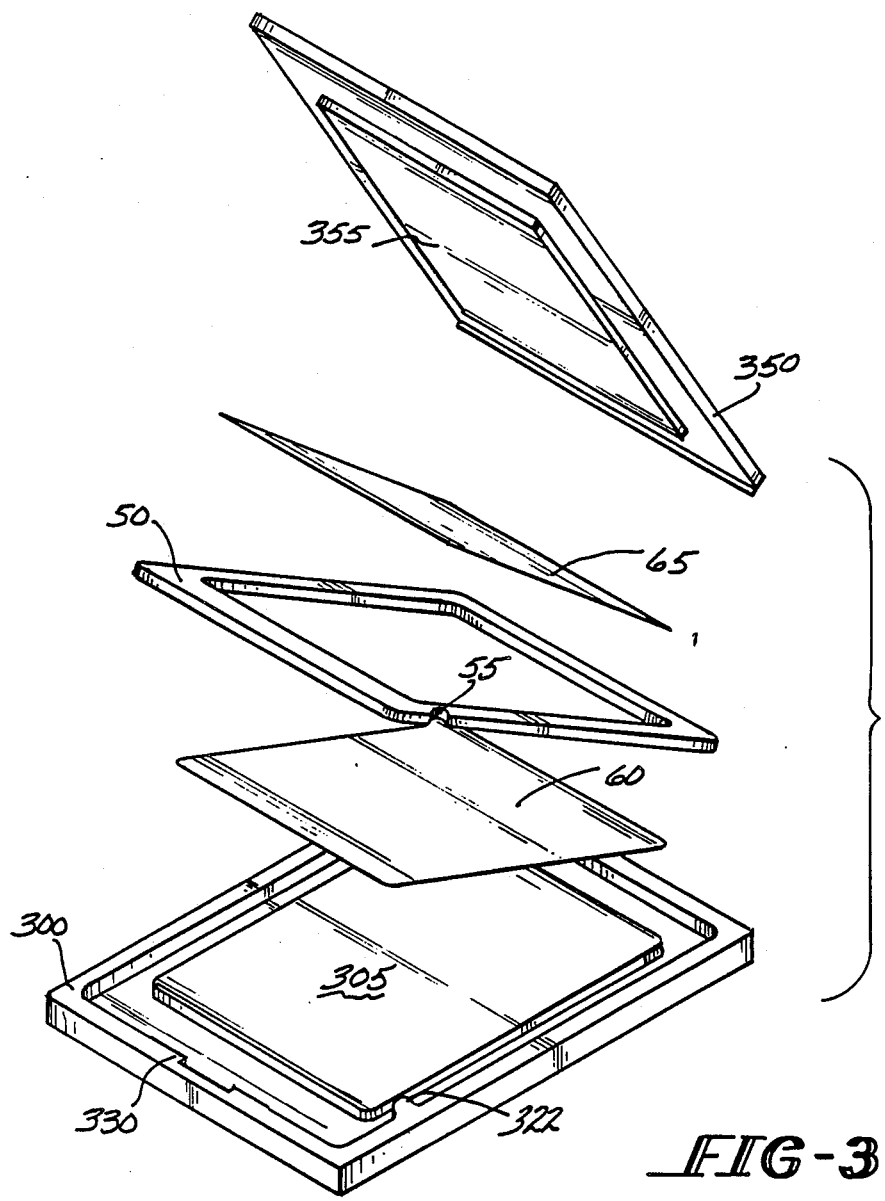
FIG. 3 is an exploded view of the various piece parts and steps at the imaging station.

FIG. 3 illustrates a preferred embodiment of an imaging cassette. The cassette consists of a light-tight container having base unit 300 and lid 350. Base unit 300 includes raised platform 305 constructed to conform to the inner dimensions of blot frame 50. The cassette is constructed of an opaque material such as sheet metal or plastic. Platform 305 is constructed of spongy foam rubber or other suitable material to provide a secure fit between frame 50 and the cassette. In operation, an appropriately-sized x-ray film 60 is placed on platform 305 and blot frame 50 is set on top of it. In the preferred embodiment illustrated, the frame is snapped in place by pressing it down past spring pressed button 330, that serves to hold the frame rigidly in place in combination with the cooperating groove 55 and projection 322. A second x-ray film 65 is then placed on top of the blot frame. When lid 350 is closed, platform 355 in the lid unit presses down against the second film, sandwiching the blot between the two films securely and in light tight fashion. After an appropriate time, the cassette is opened and the top film removed for development. In this operation it is not necessary, or even possible, to disturb the relative positions of the blot and bottom film 60. It can therefore be appreciated that the use of a framing member provides a much simpler and effective means of imaging blots than is afforded by current procedures.

Another benefit of the blot frame is that it allows for the convenient long- or short-term storage of the blots Some membranes themselves are rather brittle, and easily broken, and all membranes are easily contaminated, so storing the unframed membranes is difficult. However, it is quite simple to store the blot-frame assembly in such a way to prevent damage and contamination.

The framed blots may be conveniently stored in the unit illustrated in FIG. 2. It is provided with a watertight seal around its lid by use of gasket 210 or other appropriate means. The interior dimensions of the chamber conform to the dimensions of blot frame 50, and membrane 51 is held suspended away from all interior walls of the chamber. In this way, th blot never contacts the walls of the chamber, preventing contamination or physical buffeting as the blot is transported about the laboratory.

In use, the blot frame may be stored in a buffer solution, under vacuum or under an inert atmosphere, as deemed appropriate by the operator. The use of the blot frame thus allows for the convenient storage of the prepared blot, in a contamination-free environment suitable to the needs of the researcher and in a manner protected from physical damage.

It can be seen that the steps of blotting, hybridization, imaging, and storage are coordinated into a streamlined system by introducing the use of a framing member as a carrier piece. The increased ease of handling greatly reduces the labor required as compared to current procedures, and the lock-and-key fit between the frame and each successive step allows for a degree of uniformity and reproducibility in the geometry of the blot that is not possible using current techniques. In addition, the steps of blotting and hybridization derive unexpected benefits through the use of such a framing member, making them significantly more efficient. Finally, the introduction of a framing member provides the basis for automating many of the steps in the generation and analysis of blots.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. In combination, a transfer membrane, a transfer membrane support means whereby said transfer membrane is handled and a receptacle for receiving the support means for orienting the support means and the transfer membrane relative to the receptacle comprising:
   a protuberance located on one of the support means and the receptacle and a mating indentation located on the other of said support means and said receptacle to insure proper orientation of said transfer membrane.

2. The combination of claim 1 in which the receptacle is formed with a stepped interior side wall or shoulder providing a socket for said support means whereby the transfer membrane is suspended free of all surfaces of said receptacle.

3. The combination of claim 2 in which the receptacle is provided with a closure overlaying the support means and its transfer membrane, said stepped shoulder being dimensioned to suspend said support means so that said transfer membrane is free of contact with said closure.

4. In combination, a transfer membrane, a transfer membrane support means and a receptacle,
   a recess in said receptacle for receiving and supporting said membrane support means,
   a protuberance located on one of the support means and the receptacle and a mating indentation located on the other of said support means and said receptacle to said transfer membrane.

5. The combination of claim 4 in which the support means is formed with an indentation and the receptacle is formed with a protuberance to effect said keying.

6. The combination of claim 4 in which the receptacle is formed with a stepped interior sidewall or shoulder providing a socket for peripheral portions of said support means whereby central portions of said support means including said transfer membrane are suspended free of said sidewall.

7. In the art of processing biological components which can be attached to a transfer membrane for subsequent evaluation, an apparatus for facilitating handling said membrane comprising:
   a transfer membrane having top and bottom surfaces,
   support means attached to at least a portion of one of said surfaces of said transfer membrane to form with said membrane a composite, single piece part whereby the membrane is handled conveniently in said composite, single piece part arrangement.

8. The apparatus of claim 7 in which the support means includes a flat, rigid peripheral frame.

9. In the art of processing biological components which can be attached to a transfer membrane for subsequent evaluation at a plurality of processing stations, an apparatus for facilitating handling said membrane at each station comprising:
   a transfer membrane having top and bottom surfaces,
   a rigid support means attached to at least a portion of the transfer membrane to form with said membrane a composite, single piece part whereby said membrane in said single piece part configuration can be introduced into selected processing stations to carry out a variety of procedures to accomplish preparative, qualitative or quantitative treatment of biological components of interest.

10. An apparatus for utilizing a transfer membrane in processing biological components wherein the membrane is transported to and from a plurality of processing stations comprising:
    a transfer membrane having top and bottom surfaces and a peripheral edge,
    a rigid support means secured to at least a portion of the peripheral edge of the transfer membrane to create a composite, single piece part whereby said support means is operable to facilitate transfer of the membrane to and from said processing stations.

* * * * *

UNITED STATES PATENT AND TRADEMARK OFFICE
CERTIFICATE OF CORRECTION

PATENT NO. : 4,913,791
DATED : April 3, 1990
INVENTOR(S) : Stanley M. Hurd et al.

It is certified that error appears in the above-identified patent and that said Letters Patent is hereby corrected as shown below:

In Column 5, lines 50 and 51, "application" should read --patent--.

In Column 5, line 60, "blorting" should read --blotting--.

In Column 8, line 12, "th" should read --the--.

In Column 8, line 30, "blot" should read --blots--.

In Column 9, claim 4, line 8, insert --ensure proper orientation of-- after "tacle to".

Signed and Sealed this

Nineteenth Day of March, 1991

Attest:

HARRY F. MANBECK, JR.

*Attesting Officer*  *Commissioner of Patents and Trademarks*